(12) United States Patent
Kwak et al.

(10) Patent No.: US 7,951,174 B2
(45) Date of Patent: May 31, 2011

(54) ADJUSTABLE BONE SCREW ASSEMBLY

(75) Inventors: Seung Kyu Daniel Kwak, Grafton, MA (US); Nam T. Chao, Marlborough, MA (US); Andrea Burke, Hudson, MA (US)

(73) Assignee: DePuy Spine, Inc., Raynham, MA (US)

( * ) Notice: Subject to any disclaimer, the term of this patent is extended or adjusted under 35 U.S.C. 154(b) by 0 days.

(21) Appl. No.: 12/755,484

(22) Filed: Apr. 7, 2010

(65) Prior Publication Data

US 2010/0198273 A1 Aug. 5, 2010

Related U.S. Application Data

(63) Continuation of application No. 11/255,440, filed on Oct. 21, 2005, now Pat. No. 7,722,651.

(51) Int. Cl.
*A61B 17/70* (2006.01)
(52) U.S. Cl. ........................................ 606/270
(58) Field of Classification Search .............. 606/246, 606/251, 257, 264–265, 270, 300–309
See application file for complete search history.

(56) References Cited

U.S. PATENT DOCUMENTS

| | | | |
|---|---|---|---|
| 2,669,896 A | 2/1954 | Clough | |
| 2,952,285 A | 9/1960 | Roosli | |
| 3,604,487 A | 9/1971 | Gilbert | |
| 4,363,250 A | 12/1982 | Suga | |
| 4,733,657 A | 3/1988 | Kluger | |
| 4,743,260 A | 5/1988 | Burton | |
| 4,887,596 A | 12/1989 | Sherman | |
| 4,957,495 A | 9/1990 | Kluger et al. | |
| 4,987,892 A | 1/1991 | Krag et al. | |
| 5,005,562 A | 4/1991 | Cotrel et al. | |
| 5,067,955 A | 11/1991 | Cotrel | |
| 5,092,866 A | 3/1992 | Breard et al. | |
| 5,120,171 A | 6/1992 | Lasner | |
| 5,176,678 A | 1/1993 | Tsou | |

(Continued)

FOREIGN PATENT DOCUMENTS

DE 3923996 A1 1/1991

(Continued)

OTHER PUBLICATIONS

Wiltse, Leon L. et al., "History of Pedicle Screw Fixation of the Spine," Spine, State of the Art Reviews, vol. 6(1):1-10 (1992).

(Continued)

*Primary Examiner* — Thomas C Barrett
*Assistant Examiner* — Sameh Boles
(74) *Attorney, Agent, or Firm* — Nelson Mullins Riley & Scarborough LLP; Kevin J. Canning

(57) ABSTRACT

A bone screw assembly includes a screw body, including anchor portion and rod-receiving portion, and a rod seat movably mounted in the screw body to allow for controlled angulation between a spinal connection element disposed in the rod seat and the screw body. The rod seat is pivotable in one or more selected directions about one or more axes relative to the screw body. The rod seat may include a first lower rod seat element disposed in a recess of the screw body having a cylindrical bottom surface to facilitate pivoting in a first direction. A second lower rod seat element is stacked on the first lower rod seat element and has a conical bottom surface abutting a top surface of the first lower rod seat element to facilitate pivoting in a second direction.

17 Claims, 9 Drawing Sheets

U.S. PATENT DOCUMENTS

| | | |
|---|---|---|
| 5,176,680 A | 1/1993 | Vignaud et al. |
| 5,181,971 A | 1/1993 | Ohtsuka |
| 5,190,543 A | 3/1993 | Schlapfer |
| 5,219,349 A | 6/1993 | Krag et al. |
| 5,226,766 A | 7/1993 | Lasner |
| 5,263,939 A | 11/1993 | Wortrich |
| 5,282,801 A | 2/1994 | Sherman |
| 5,282,863 A | 2/1994 | Burton |
| 5,330,474 A | 7/1994 | Lin |
| 5,360,431 A | 11/1994 | Puno et al. |
| 5,385,565 A | 1/1995 | Ray |
| 5,387,213 A | 2/1995 | Breard et al. |
| 5,415,661 A | 5/1995 | Holmes |
| 5,468,241 A | 11/1995 | Metz-Stavenhagen et al. |
| 5,487,744 A | 1/1996 | Howland |
| 5,499,983 A | 3/1996 | Hughes |
| 5,501,684 A | 3/1996 | Schlapfer et al. |
| 5,520,689 A | 5/1996 | Schlapfer et al. |
| 5,536,127 A | 7/1996 | Pennig |
| 5,536,268 A | 7/1996 | Griss |
| 5,540,688 A | 7/1996 | Navas |
| 5,549,608 A | 8/1996 | Errico et al. |
| 5,591,166 A | 1/1997 | Bernhardt et al. |
| 5,649,931 A | 7/1997 | Bryant et al. |
| 5,667,513 A | 9/1997 | Torrie et al. |
| 5,672,176 A | 9/1997 | Biedermann et al. |
| 5,797,911 A | 8/1998 | Sherman et al. |
| 5,879,350 A | 3/1999 | Sherman et al. |
| 5,882,350 A | 3/1999 | Ralph et al. |
| 5,885,285 A | 3/1999 | Simonson |
| RE36,211 E | 5/1999 | Nonomura |
| RE36,221 E | 6/1999 | Breard et al. |
| 5,910,141 A | 6/1999 | Morrison et al. |
| 5,951,555 A | 9/1999 | Rehak et al. |
| 5,964,760 A | 10/1999 | Richelsoph |
| 5,989,250 A | 11/1999 | Wagner et al. |
| 5,989,254 A | 11/1999 | Katz |
| 6,050,997 A | 4/2000 | Mullane |
| 6,063,090 A | 5/2000 | Schlapfer |
| 6,074,391 A | 6/2000 | Metz-Stavenhagen et al. |
| 6,090,110 A | 7/2000 | Metz-Stavenhagen |
| 6,090,113 A | 7/2000 | Le Couedic et al. |
| 6,139,549 A | 10/2000 | Keller |
| 6,146,383 A | 11/2000 | Studer et al. |
| 6,183,472 B1 | 2/2001 | Lutz |
| 6,204,060 B1 | 3/2001 | Mehtali et al. |
| 6,254,602 B1 | 7/2001 | Justis |
| 6,261,287 B1 | 7/2001 | Metz-Stavenhagen |
| 6,280,442 B1 | 8/2001 | Barker et al. |
| 6,280,443 B1 | 8/2001 | Gu et al. |
| 6,302,888 B1 | 10/2001 | Mellinger et al. |
| 6,309,389 B1 | 10/2001 | Baccelli |
| 6,368,321 B1 | 4/2002 | Jackson |
| 6,379,357 B1 | 4/2002 | Bernstein et al. |
| 6,423,065 B2 | 7/2002 | Ferree |
| 6,440,133 B1 | 8/2002 | Beale et al. |
| 6,440,137 B1 | 8/2002 | Horvath et al. |
| 6,443,953 B1 | 9/2002 | Perra et al. |
| 6,478,798 B1 | 11/2002 | Howland |
| 6,537,276 B2 | 3/2003 | Metz-Stavenhagen |
| 6,540,748 B2 | 4/2003 | Lombardo |
| 6,565,567 B1 | 5/2003 | Haider |
| 6,597,279 B1 | 7/2003 | Haraguchi |
| 6,623,485 B2 | 9/2003 | Doubler et al. |
| 6,648,888 B1 | 11/2003 | Shluzas |
| 6,660,006 B2 | 12/2003 | Markworth et al. |
| 6,689,137 B2 | 2/2004 | Reed |
| 6,692,500 B2 | 2/2004 | Reed |
| 6,695,843 B2 | 2/2004 | Biedermann et al. |
| 6,716,214 B1 | 4/2004 | Jackson |
| 6,733,502 B2 | 5/2004 | Altarac et al. |
| 6,743,231 B1 | 6/2004 | Gray et al. |
| 6,749,613 B1 | 6/2004 | Conchy et al. |
| 6,755,829 B1 | 6/2004 | Bono et al. |
| 6,783,527 B2 | 8/2004 | Drewry et al. |
| 6,800,078 B2 | 10/2004 | Reed |
| 6,800,079 B2 | 10/2004 | Reed |
| 6,837,889 B2 | 1/2005 | Shluzas |
| 6,964,666 B2 | 11/2005 | Jackson |
| 7,179,261 B2 | 2/2007 | Sicvol et al. |
| 7,322,979 B2 | 1/2008 | Crandall et al. |
| 7,455,685 B2 | 11/2008 | Justis |
| 7,465,306 B2 | 12/2008 | Pond, Jr. et al. |
| 7,666,189 B2 | 2/2010 | Gerber et al. |
| 7,766,944 B2 | 8/2010 | Metz-Stavenhagen |
| 2001/0020169 A1 | 9/2001 | Metz-Stavenhagen |
| 2002/0035366 A1 | 3/2002 | Walder et al. |
| 2002/0082599 A1 | 6/2002 | Crandall et al. |
| 2002/0133155 A1 | 9/2002 | Ferree |
| 2002/0143341 A1 | 10/2002 | Biedermann et al. |
| 2002/0173789 A1 | 11/2002 | Howland |
| 2003/0073995 A1 | 4/2003 | Reed |
| 2003/0083657 A1 | 5/2003 | Drewry et al. |
| 2003/0088248 A1 | 5/2003 | Reed |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0171749 A1 | 9/2003 | Le Couedic et al. |
| 2003/0176861 A1 | 9/2003 | Reed |
| 2003/0191470 A1 | 10/2003 | Ritland |
| 2003/0203488 A1 | 10/2003 | Mehtali et al. |
| 2003/0220642 A1 | 11/2003 | Freudiger |
| 2003/0220643 A1 | 11/2003 | Ferree |
| 2004/0002708 A1 | 1/2004 | Ritland |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0147937 A1 | 7/2004 | Dunbar et al. |
| 2004/0158258 A1 | 8/2004 | Bonati et al. |
| 2004/0172025 A1 | 9/2004 | Drewry et al. |
| 2004/0181224 A1 | 9/2004 | Biedermann et al. |
| 2004/0186473 A1 | 9/2004 | Cournoyer et al. |
| 2004/0204711 A1 | 10/2004 | Jackson |
| 2004/0225289 A1 | 11/2004 | Biedermann et al. |
| 2004/0267260 A1 | 12/2004 | Mack et al. |
| 2004/0267275 A1 | 12/2004 | Cournoyer et al. |
| 2005/0033291 A1 | 2/2005 | Ebara |
| 2005/0033295 A1 | 2/2005 | Wisnewski |
| 2005/0065514 A1 | 3/2005 | Studer |
| 2005/0065515 A1 | 3/2005 | Jahng |
| 2005/0065516 A1 | 3/2005 | Jahng |
| 2005/0066514 A1 | 3/2005 | Chau et al. |
| 2005/0070917 A1 | 3/2005 | Justis |
| 2005/0085815 A1 | 4/2005 | Harms et al. |
| 2005/0131408 A1 | 6/2005 | Sicvol et al. |
| 2005/0131422 A1 | 6/2005 | Anderson et al. |
| 2005/0159650 A1 | 7/2005 | Raymond et al. |
| 2005/0192573 A1 | 9/2005 | Abdelgany et al. |
| 2005/0192589 A1 | 9/2005 | Raymond et al. |
| 2005/0222570 A1 | 10/2005 | Jackson |
| 2005/0228376 A1 | 10/2005 | Boomer et al. |
| 2005/0245928 A1 | 11/2005 | Colleran et al. |
| 2005/0261687 A1 | 11/2005 | Garamszegi et al. |
| 2005/0283244 A1 | 12/2005 | Gordon |
| 2005/0288668 A1 | 12/2005 | Brinkhaus |
| 2006/0036255 A1 | 2/2006 | Pond et al. |
| 2006/0149236 A1 | 7/2006 | Barry |
| 2006/0155277 A1 | 7/2006 | Metz-Stavenhagen |
| 2006/0173454 A1 | 8/2006 | Spitler et al. |
| 2006/0195092 A1 | 8/2006 | Barry |
| 2006/0200131 A1 | 9/2006 | Chao et al. |
| 2006/0200132 A1 | 9/2006 | Chao et al. |
| 2006/0217735 A1 | 9/2006 | MacDonald et al. |
| 2006/0229614 A1 | 10/2006 | Foley et al. |
| 2007/0162009 A1 | 7/2007 | Chao et al. |
| 2007/0162010 A1 | 7/2007 | Chao et al. |
| 2008/0195159 A1 | 8/2008 | Kloss et al. |

FOREIGN PATENT DOCUMENTS

| | | |
|---|---|---|
| DE | 4107480 A1 | 9/1992 |
| DE | 10005385 A1 | 8/2001 |
| DE | 10005386 A1 | 8/2001 |
| DE | 20207851 U1 | 11/2002 |
| EP | 0381588 B2 | 8/1990 |
| EP | 0441729 B1 | 8/1991 |
| EP | 0487895 A1 | 6/1992 |
| EP | 0572790 B1 | 12/1993 |

| | | | |
|---|---|---|---|
| EP | 0592266 A1 | 4/1994 |
| EP | 328883 B1 | 7/1994 |
| EP | 0669109 B1 | 8/1995 |
| EP | 558883 B1 | 7/1997 |
| EP | 0880344 B1 | 12/1998 |
| EP | 0885598 A2 | 12/1998 |
| EP | 0951246 B1 | 10/1999 |
| EP | 1023873 A2 | 8/2000 |
| EP | 1090595 A2 | 4/2001 |
| EP | 784693 B1 | 10/2001 |
| EP | 1295566 A1 | 3/2003 |
| EP | 1364622 B1 | 11/2003 |
| WO | 90/02527 A1 | 3/1990 |
| WO | 9822033 A1 | 5/1998 |
| WO | 98/25534 A1 | 6/1998 |
| WO | 9944527 A1 | 9/1999 |
| WO | 01/45576 A1 | 6/2001 |
| WO | 02/07622 A1 | 1/2002 |
| WO | 02/102259 A2 | 12/2002 |
| WO | 03/007828 A1 | 1/2003 |
| WO | 03/032863 A2 | 4/2003 |
| WO | 03/049629 A1 | 6/2003 |
| WO | 2004/019755 A2 | 3/2004 |
| WO | 2004/034916 A1 | 4/2004 |
| WO | 2005/013839 A2 | 2/2005 |
| WO | 2005/030065 A1 | 4/2005 |
| WO | 2005/044117 A2 | 5/2005 |
| WO | 2005/044123 A1 | 5/2005 |
| WO | 2006/084443 A1 | 8/2006 |

OTHER PUBLICATIONS

International Search Report and Written Opinion for Application No. PCT/US06/40621, dated May 18, 2007.
International Search Report for Application No. PCT/US06/40621, dated May 18, 2007.
International Search Report for Application No. PCT/US06/05811, dated Sep. 13, 2007.
European Office Action for Application No. 06736870, dated Dec. 18, 2009.
European Office Action for Application No. 06735464.7, dated Apr. 14, 2010.

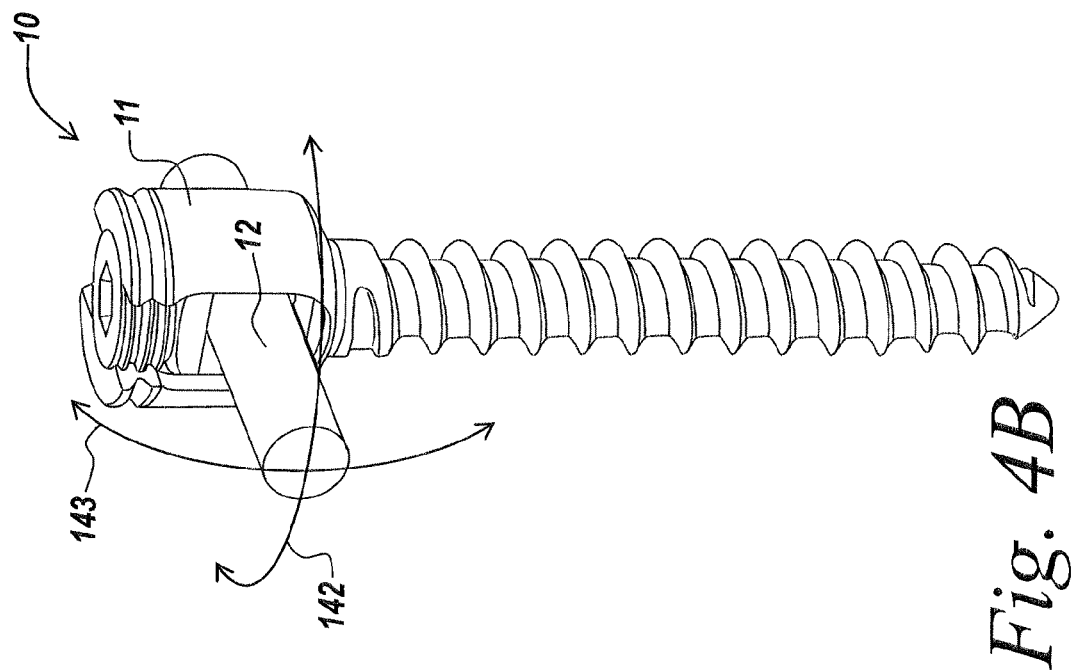
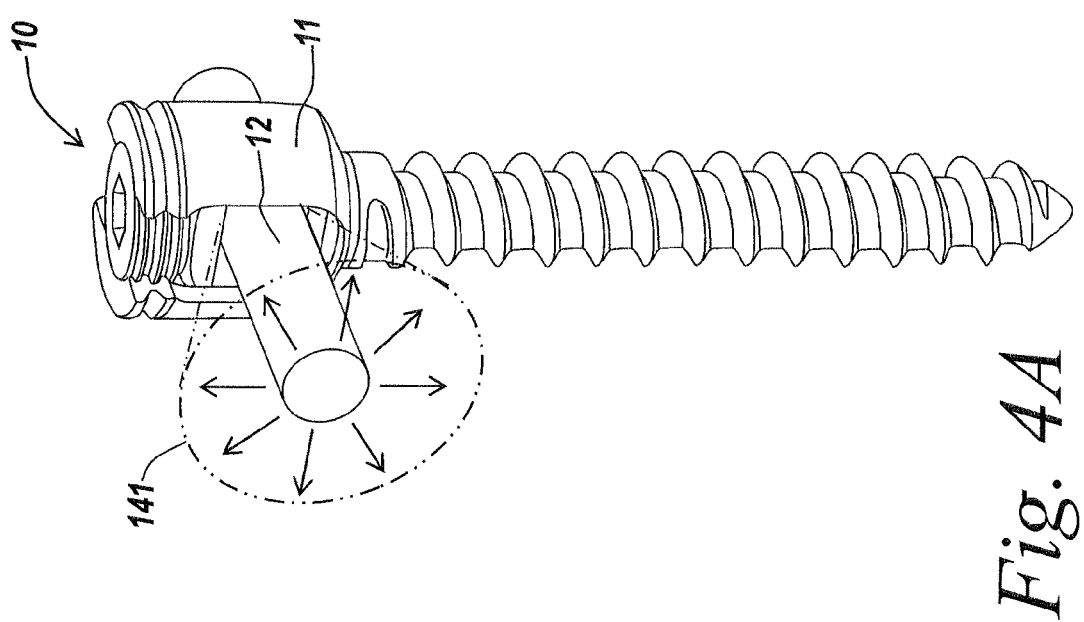

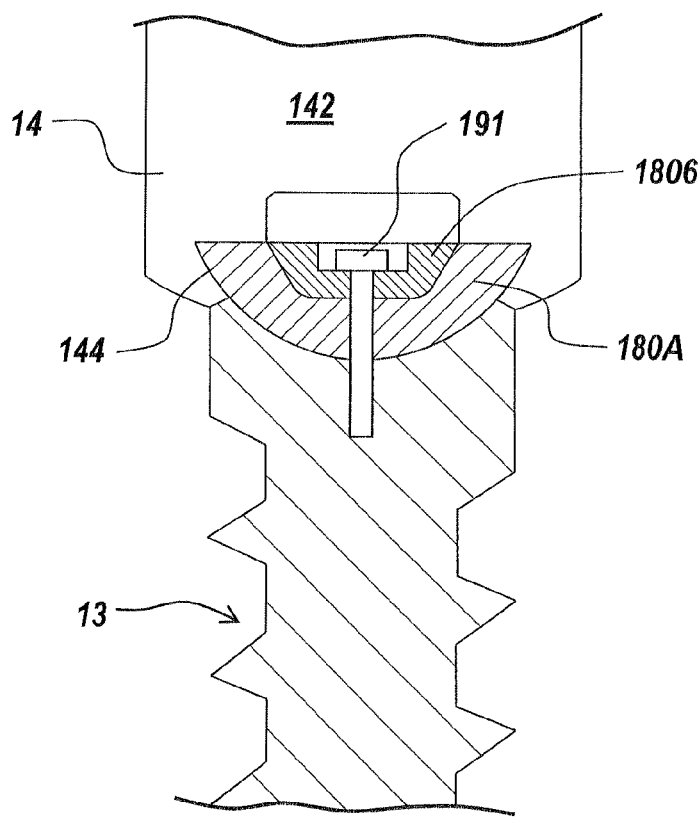
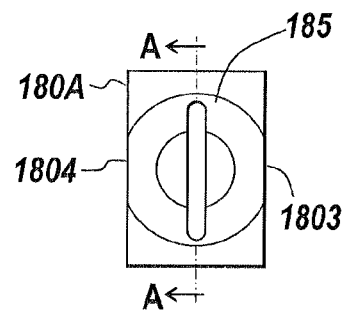
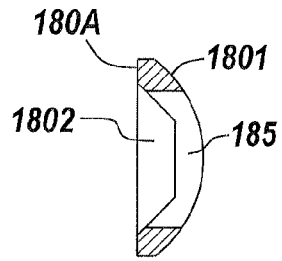
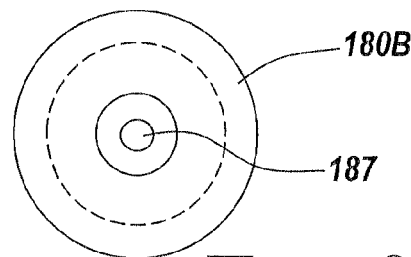
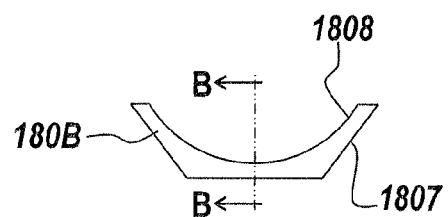
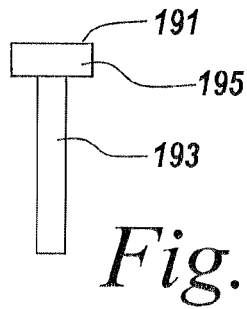
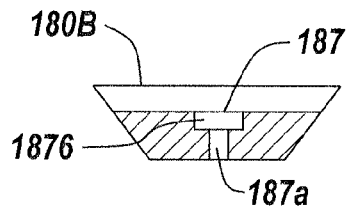
Fig. 7
Fig. 8A
Fig. 8B
Fig. 9A
Fig. 9B
Fig. 10
Fig. 9C

ADJUSTABLE BONE SCREW ASSEMBLY

RELATED APPLICATION

This application is a continuation application of U.S. patent application Ser. No. 11/255,440, entitled "ADJUSTABLE BONE SCREW ASSEMBLY," filed Oct. 21, 2005, the contents of which are hereby incorporated by reference.

FIELD OF THE INVENTION

The present invention relates to spinal connection devices used in orthopedic surgery. More particularly, the present invention relates to a bone screw for coupling a spinal rod to a bone, such as the pedicle.

BACKGROUND OF THE INVENTION

Spinal fixation systems may be used in surgery to align, adjust and/or fix portions of the spinal column, i.e., vertebrae, in a desired spatial relationship relative to each other. Many spinal fixation systems employ a spinal rod for supporting the spine and for properly positioning components of the spine for various treatment purposes. Vertebral anchors, comprising pins, bolts, screws, and hooks, engage the vertebrae and connect the supporting rod to different vertebrae. The size, length and shape of the cylindrical rod depend on the size, number and position of the vertebrae to be held in a desired spatial relationship relative to each other by the apparatus.

Spinal fixation elements can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a spinal fixation element-receiving portion, which, in spinal rod applications, is usually in the form of a U-shaped slot formed in the head portion for receiving the rod. A set-screw, plug, cap or similar type of closure mechanism is used to lock the rod into the rod-receiving portion of the pedicle screw. In use, the shank portion of each screw is then threaded into a vertebra, and once properly positioned, a spinal fixation rod is seated through the rod-receiving portion of each screw. The rod is locked into place by tightening a cap or similar type of closure mechanism to securely interconnect each screw and the fixation rod. Other anchoring devices also include hooks and other types of bone screws.

Monoaxial screws are a type of screw in which the longitudinal axis of the threaded shank is fixed relative to the head portion, or rod slot. The longitudinal axis of the threaded shank may be aligned with the longitudinal axis of the head portion, and/or the threaded shank extends at a fixed angle relative to the head. In fixed pedicle screws, which are used in the pedicle region of the vertebra, the threaded shank is rigidly connected to or integrally formed with the head such that the orientation of the threaded shank is fixed with respect to the head.

Polyaxial pedicle screws have been designed to allow angulation of one portion of the screw relative to another portion of the screw and the spinal fixation element coupled to one portion of the screw. For example, polyaxial pedicle screws allow for a shaft portion to pivot relative to a rod-receiving portion in all directions about a 360° arc around the rod-receiving portion. Polyaxial screws may be useful for positioning bone anchors on adjacent vertebrae, when the close proximity of adjacent vertebrae can result in interference between the bone anchors. Polyaxial screws allow for pivoting of the screws in any direction out of alignment with each other to avoid such interference.

An example of such a polyaxial pedicle screw assembly is described in detail in U.S. Patent Application Publication Number US 2004/0186473 entitled "Spinal Fixation Devices of Improved Strength and Rigidity", U.S. Patent Application Publication Number US 2004/0181224 entitled "Anchoring Element for Use in Spine or Bone Surgery, Methods for Use and Production Thereof" and U.S. Patent Application Publication Number US 2003/0100896, entitled "Element With a Shank and a Holding Element Connected to It for Connecting to a Rod", the contents of which are herein incorporated by reference.

Polyaxial and multi-axial screws, which allow the screw shank to pivot in all directions about the head portion, can be difficult to control and often result in movement of the screw shank in planes in which movement is not desirable. For example, during vertebral body rotation maneuvers, which require application of force to the screw head, it is not desirable for the screw shank to move relative to the screw head.

In addition, prior art bone screw systems are not optimized for non-fusion systems, which may employ flexible rods. Without the support of fused bones, non-fusion systems must withstand the applied load for a longer time, even for the lifetime of a patient.

An additional complication of non-fusion stabilization systems is a loosening between the screw and bone. Monoaxial and polyaxial screws of the prior art tend to have a relatively large distance between the center of the rod and the vertebral body surface, resulting in a relatively large moment applied to the screw body by the rod when the screw is implanted, leading to loosening and/or breakage.

SUMMARY OF THE INVENTION

The present invention provides an adjustable bone screw assembly that provides for controlled adjustment of a spinal connection element, such as a spinal rod, received in a body of the bone screw assembly relative to the body of the bone screw. The adjustable bone screw assembly may allow the spinal connection element received in a receiving portion of the assembly to pivot in at least two directions about two different axes, while limiting movement in other selected directions. In addition, the bone screw assembly may reduce a distance between a center of a rod connected to the bone screw assembly and the vertebral bone surface secured by the bone screw assembly. The adjustable bone screw assembly thus allows for sufficient adjustability for rod placement and orientation, while reducing the moment applied on the screw.

According to a first aspect of the invention, a bone anchor assembly comprises a bone anchor having a distal shaft extending along a longitudinal axis configured to engage bone, a proximal head portion and a rod seat disposed within the proximal head portion for seating the spinal rod, wherein the rod seat allows for a controlled pivoting movement of the spinal rod about two selected axes in two directions relative to the head portion.

According to another aspect of the invention, a bone anchor assembly comprises a bone anchor having a distal shaft extending along a longitudinal axis configured to engage bone and a proximal head, a first lower rod seat element disposed in a recess of the proximal head and having a cylindrical bottom surface and a second lower rod seat element stacked on the first lower rod seat element. The second lower rod seat element has a conical bottom surface abutting a top surface of the first lower rod seat element and an upper surface for seating the spinal rod.

A retaining means may movably retain the first lower rod seat element in the recess. A retaining means may rotatably retain the second lower rod seat element on the first lower rod seat element.

According to another aspect of the invention, a bone anchor assembly comprises a bone anchor having a distal shaft extending along a longitudinal axis configured to engage bone and a proximal head and a rod seat disposed in the proximal head for seating a spinal rod. The rod seat includes a top surface for receiving the spinal rod and a conical bottom surface disposed in a corresponding recess to allow pivoting of the spinal rod about a longitudinal axis of the conical bottom surface.

According to another aspect of the invention, a bone anchor assembly, comprises a bone anchor portion having a distal shaft extending along a longitudinal axis configured to engage bone and a head portion fixed to a proximal end of the bone anchor portion. The head portion is configured to receive a spinal rod and allow for a controlled pivoting movement of the spinal rod about two selected axes in two directions relative to the head portion.

According to another aspect of the invention, a method of connecting two vertebrae is provided. The method comprises the steps of inserting a first portion of a spinal rod in a first rod-receiving portion of a first bone screw assembly connected to a first vertebra, adjusting an orientation of the spinal rod relative to the first rod-receiving portion in a first direction and adjusting an orientation of the spinal rod relative to the first rod-receiving portion in a second direction.

BRIEF DESCRIPTION OF THE DRAWINGS

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions.

FIGS. 4A and 4B illustrate possible ranges of motion of the spinal rod relative to the bone screw body according to different embodiments of the invention.

FIG. 7 illustrates a biaxial bone screw assembly of an embodiment of the invention including a retaining pin for coupling the first lower rod seat element and the second lower rod seat element.

FIGS. 8A-8B illustrates an embodiment of the first lower rod seat element of the biaxial bone screw assembly of FIG. 7.

FIG. 9A-9C illustrates an embodiment of the second lower rod seat element of the biaxial bone screw assembly of FIG. 7.

FIG. 10 illustrates the retaining pin employed by the biaxial bone screw assembly of FIG. 7.

DETAILED DESCRIPTION OF THE INVENTION

The present invention provides an improved bone screw assembly in a spinal connection system. One skilled in the art will recognize that the invention is not limited to use in bone or in spinal surgery, and that the instrument and methods described herein can be adapted for use with any suitable surgical device to be moved into a selected position in a variety of medical procedures. The present invention will be described below relative to certain exemplary embodiments to provide an overall understanding of the principles of the structure, function, manufacture, and use of the instruments disclosed herein. Those skilled in the art will appreciate that the present invention may be implemented in a number of different applications and embodiments and is not specifically limited in its application to the particular embodiments depicted herein.

Figure 11B:
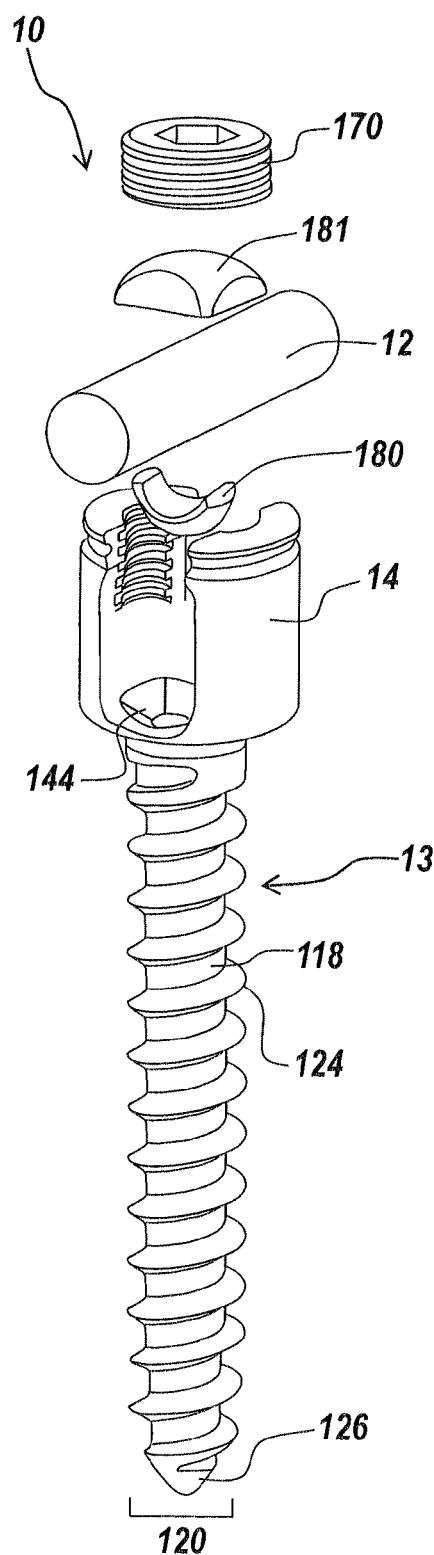
FIGS. 11A and 11B illustrate an adjustable bone screw assembly according to another embodiment of the invention.
Figure 11A:
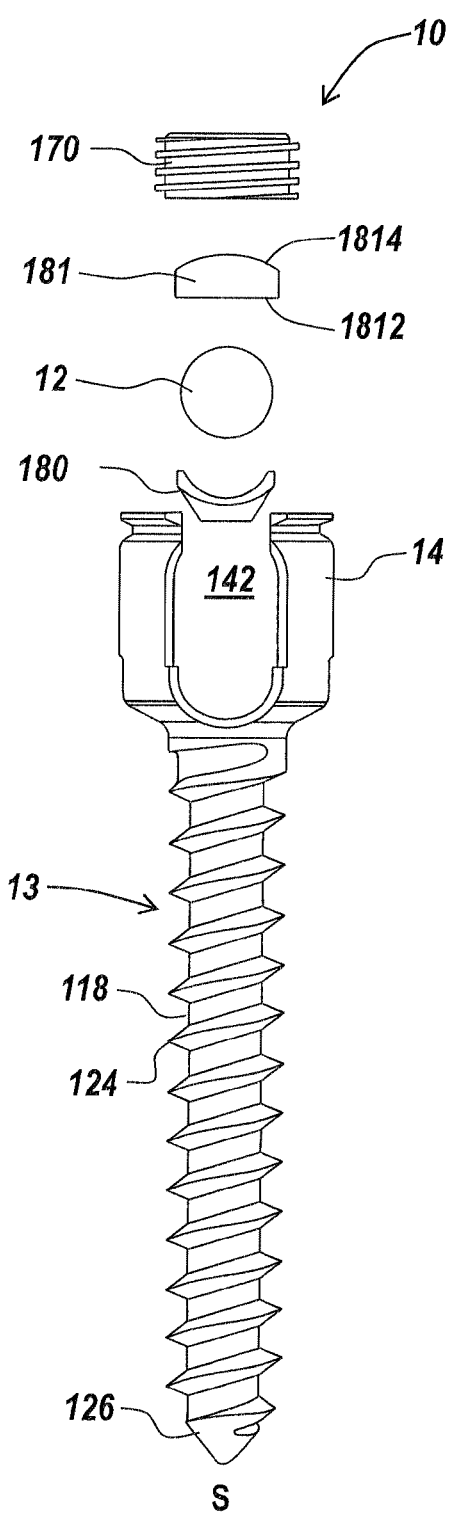

During spinal deformity surgeries, it may be necessary to de-rotate the vertebral bodies to normalize the spine. Due to varying patient anatomy, insertion of fixed angle screws, where the anchor portion of the screw extends at a fixed angle relative to the rod-receiving portion of the screw can be difficult. Polyaxial and multi-axial screws, which allow the screw shank to pivot in all directions about the rod-receiving head portion, can be difficult to control and often result in undesirable movement in certain planes. An adjustable bone screw assembly allows for angulation of a spinal rod or other implant relative to the body of the screw that receives the spinal rod or other implant therein. For example, a biaxial bone screw assembly, different embodiments of which are illustrated in FIGS. 1-10 and 12-15, allows for angulation of a spinal rod or other implant relative to the body of the screw in at least two planes, while minimizing a distance between a rod center and a surface of the bone secured by the biaxial bone screw assembly. As shown in FIGS. 11A and 11B, an adjustable bone screw assembly may be uniaxial and permit movement about a single selected axis. The adjustable bone screw assembly of the invention is not limited to a uniaxial or biaxial movement and may allow adjustment of a spinal rod or implant relative to a screw body that retains the rod or implant in any selected number of directions and about any selected number of axes.

The adjustable bone screw assembly of the present invention may allow a surgeon to rotate vertebral bodies and facilitates rod placement into the rod-receiving portion. The adjustable bone screw assembly allows for a surgeon to achieve an ideal orientation of the spinal rod relative to the bone screw, without requiring the spinal rod to have a predetermined, fixed orientation, or necessarily be perpendicular to the longitudinal axis of the screw shank.

The exemplary adjustable bone screw assemblies of the illustrative embodiments of the invention may be employed to engage one or more spinal connection elements to bone. For example, a bone screw assembly may be employed to fix a spinal plate, rod, and/or cable to a vertebra of the spine. Although the exemplary bone screw assemblies described below are designed primarily for use in spinal applications, and specifically the pedicle region of a vertebra, one skilled in the art will appreciate that the structure, features and principles of the exemplary bone screw assemblies, as well as the other exemplary embodiments described below, may be employed to couple any type of orthopedic implant to any type of bone or tissue. The bone screw assembly described herein facilitates the correction of the position, for example, the angular orientation, of the vertebra in which the bone screw is implanted, as described in U.S. patent application Ser. No. 11/073,352 entitled "Instruments and Methods for Manipulating a Vertebra", filed on Mar. 4, 2005 and U.S. patent application Ser. No. 11/073,325 (DUQ-006) file on Mar. 4, 2005, the contents of which are herein incorporated by reference.

The illustrative adjustable bone screw assembly may be used to attach a non-rigid member to bone. For example, the adjustable bone screw assembly may be used to attach a rod, ligament, bar, cable or other non-rigid member extending between and connecting two bone screws, for example for connecting superior and inferior vertebra. Alternatively, the bone screw assembly may be used to attach a rigid member to bone. While the invention will be described with respect to a bone screw assembly that receives a spinal rod that is movably about two axes relative to the bone screw assembly, the invention is not limited to spinal rods and may be used with any suitable spinal connection element to be coupled to bone.

Figure 1A:
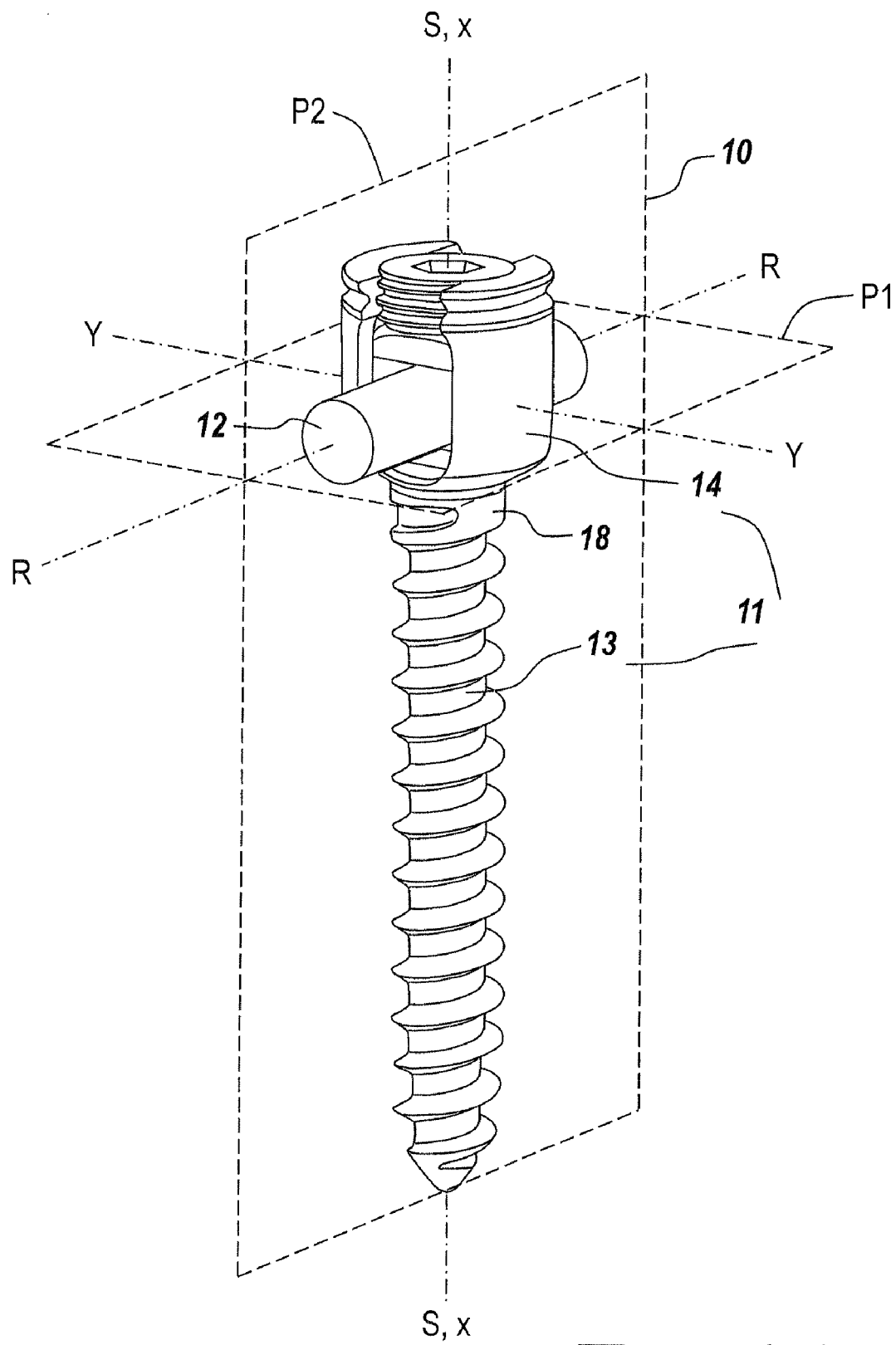
FIGS. 1A and 1B illustrate an assembled bone screw assembly including a spinal rod movably received therein according to an illustrative embodiment of the invention.
Figure 1B:
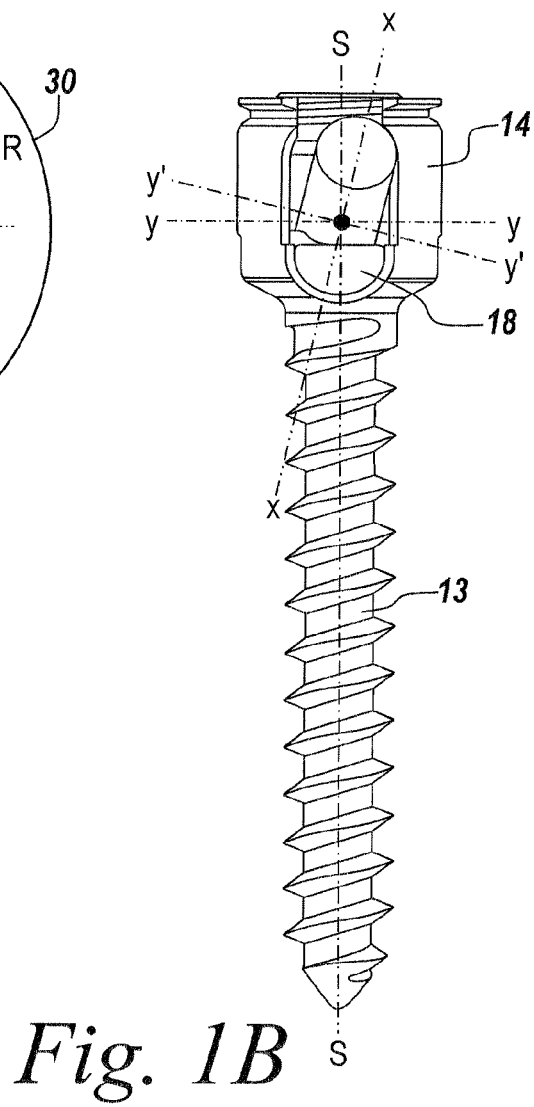

According to one aspect of the invention, a biaxial bone screw assembly 10, an embodiment of which is shown in FIGS. 1A and 1B, is provided to allow movement of a spinal rod in two directions relative to a bone screw body. The biaxial bone screw assembly 10 has a screw body 11, which includes a distal anchor portion 13 for anchoring the screw assembly to bone and a proximal head portion 14. The proximal head portion 14 may form a receiving portion, such as a rod-receiving portion, for receiving a spinal rod 12 or other spinal connection element. An adjustable rod seat 18, disposed within the head portion 14, seats the spinal rod 12, thereby coupling the spinal rod 12 to a bone anchored by the anchor portion 13. The movable rod seat 18 may alternatively be sized and configured to receive another spinal connection element in an adjustable position.

The orientation of the rod seat 18 may be selectively adjusted to controllably adjust the orientation of the spinal rod 12 relative to the body 11 of the bone screw assembly 10. Preferably, the illustrative rod seat 18 allows for pivoting of the spinal rod 12 about two separate axes in at least two directions relative to the body 11 of the screw assembly, though one skilled in the art will recognize that the rod seat 18 and spinal rod 12 of the invention may alternatively pivot about one or several axes. For example, the illustrative rod seat 18 allows the spinal rod 12 to pivot about a first axis X-X and/or a second axis Y-Y relative to the anchor portion 13 and/or head portion 14 to provide two degrees of freedom of the spinal rod position relative to the bone screw body 11.

The rod seat 18 extends along an axis R-R, which defines and corresponds to the longitudinal axis of the spinal rod 12. In a default position, the axis R-R is preferably perpendicular to the longitudinal axis S-S of the body 11, though one skilled in the art will recognize that the rod seat 18 may have any suitable default orientation.

Figure 2:
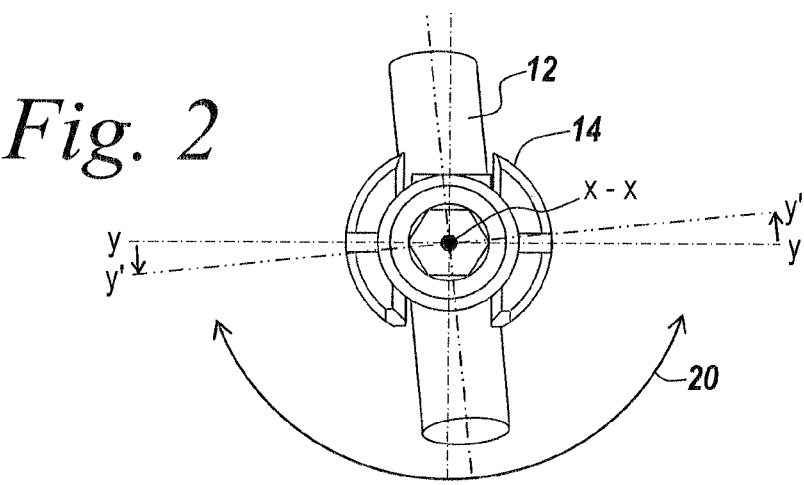
FIG. 2 is a top view of the assembled bone screw assembly, illustrating a first degree of freedom.

As shown in FIG. 2, the spinal rod 12 may pivot about axis X-X in a direction indicated by arrow 20. In the illustrative embodiment, the axis X-X extends through the center of the rod seat 18, perpendicular to the axis R-R and aligns with the longitudinal axis S-S of the screw body 11 when the rod seat 18 is in a default position, so that the spinal rod 12 sweeps through a first plane P1 shown in FIG. 1A. In this manner, the illustrative spinal rod 12 spins about the screw body 11. The illustrative first plane P1 is substantially parallel to the coronal plane of the body when the bone screw assembly 10 is employed in a patient. However, one skilled in the art will recognize that the first axis X-X about which the spinal rod 12 can pivot may have any suitable orientation and is not limited to the illustrative orientation.

Figure 3:
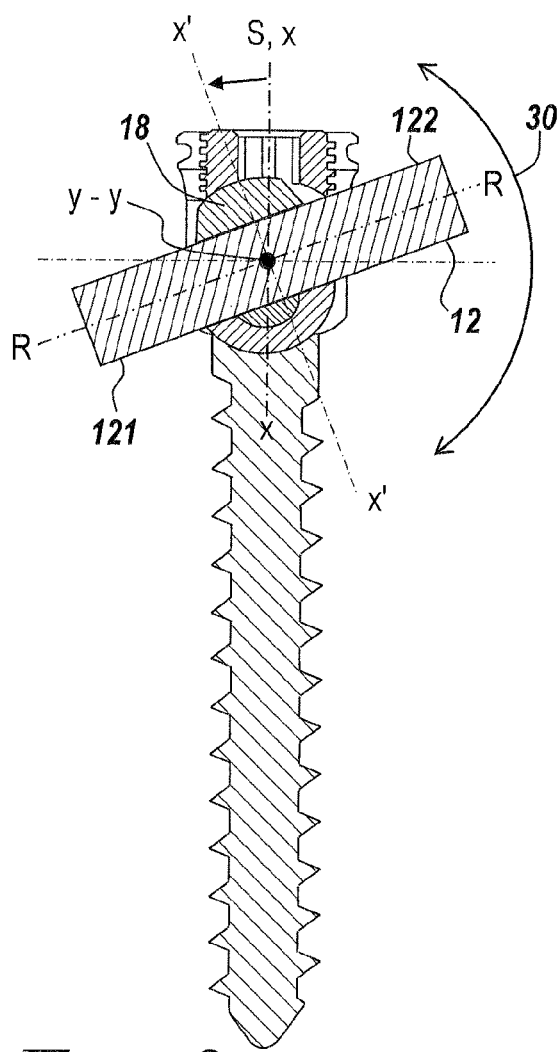
FIG. 3 is a side view of the assembled bone screw assembly, illustrating a second degree of freedom.

As shown in FIG. 3, the spinal rod 12 may also or alternatively pivot in a second plane P2 about axis Y-Y in a direction indicated by arrow 30. In the illustrative embodiment, the axis Y-Y extends substantially perpendicular to the axis X-X, the axis S-S, and the axis R-R of the spinal rod 12 when the rod seat 18 is in a default position, though one skilled in the art will recognize that the second axis about which the spinal rod 12 can pivot may have any suitable orientation. The plane P2 corresponds to the sagittal plane in a body when the illustrative biaxial bone screw assembly is implanted in the body. As shown, the adjustability about axis Y-Y allows for one end 121 of the spinal rod 12 to pivot towards the body while the other end of the spinal rod 122 pivots away from the body. However, one skilled in the art will recognize that the second axis Y-Y about which the spinal rod 12 can pivot may have any suitable orientation and is not limited to the illustrative orientation.

The adjustment about the two axes X-X and Y-Y can be mutually exclusive, or concurrent. A user may rotate the spinal rod 12 by a selected amount about only the X-X axis, only the Y-Y axis, or both. The rotation about one axis may cause the orientation of the other axis to shift, or the orientation of each axis X-X and Y-Y may be fixed independently of the orientation of the other axis. For example, as shown in FIG. 2, the rotation of the spinal rod about axis X-X may cause the axis Y-Y to shift by the amount of rotation of the spinal rod to position Y'-Y', so that the axis Y-Y remains parallel to the axis R-R. As shown in FIG. 3, the rotation of the rod 12 about axis Y-Y may cause the axis X-X to shift to the position X'-X' shown in FIG. 3. Alternatively, one or both of the axes X-X and/or Y-Y may be fixed regardless of the rotation of the spinal rod 12 about the other axis.

FIGS. 4A and 4B illustrate possible areas of movement of the spinal rod relative to the bone screw body according to different embodiments of the invention. As shown in FIG. 4A, the spinal rod 12 may pivot through a cone of motion 141 defining the possible orientations of the spinal rod 12 relative to the body 11 through rotation about the X-X and/or Y-Y axis. Alternatively, as shown in FIG. 4B, the spinal rod 12 may be confined to paths 142, 143, defined by axes X-X and Y-Y, respectively.

In addition, for cylindrical rods or other spinal connection elements, the rod 12 may be rotated about axis R-R and/or slide within the rod seat 18, providing a third degree of freedom for attaining a selected orientation of the spinal rod relative to the screw assembly 120.

Figure 5A:
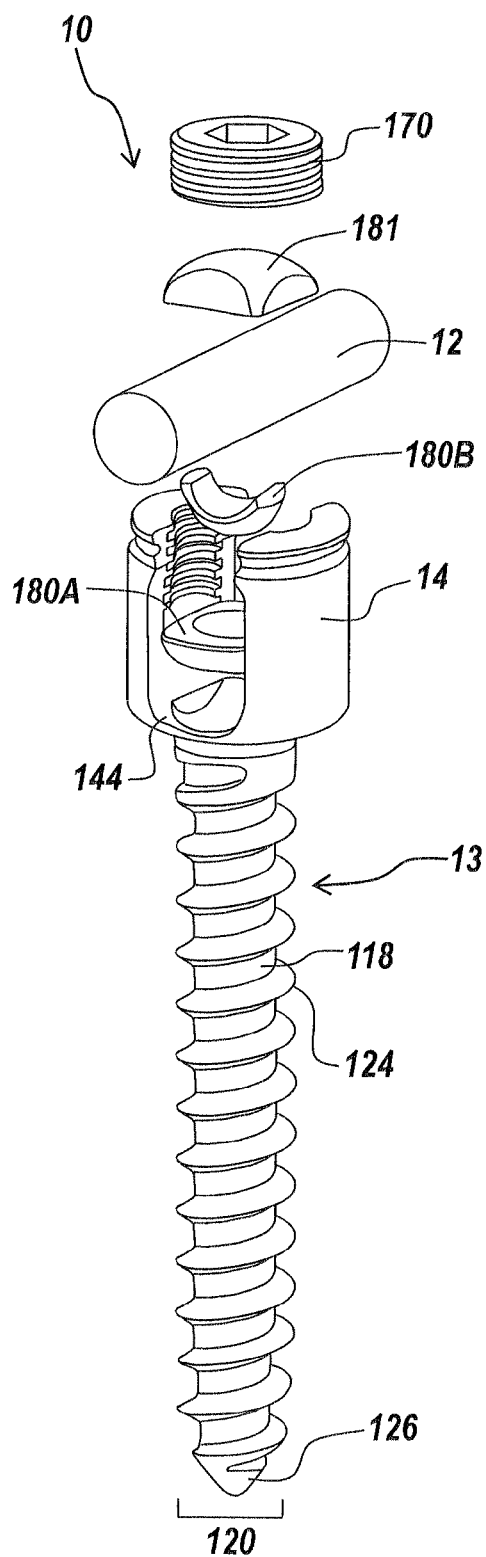
FIGS. 5A and 5B are exploded views of a biaxial bone screw assembly according to one embodiment of the invention.
Figure 5B:
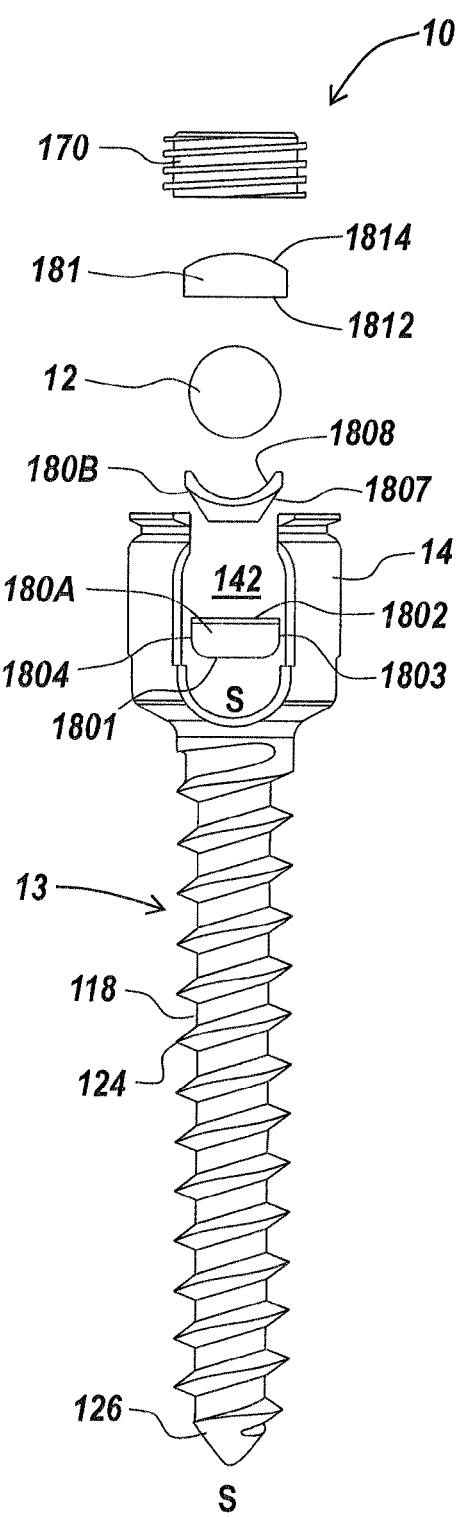

FIGS. 5A and 5B are exploded views of a biaxial bone screw assembly 10, illustrating the individual components of the assembly 10 that facilitate the biaxial adjustability according to an illustrative embodiment of the invention.

The bone anchor 13 comprises a distal shaft 118 configured to engage bone. The distal shaft 118 of the bone anchor 13 has a shaft diameter 120 and a longitudinal axis S-S. The distal shaft 118 may include one or more bone engagement mechanisms to facilitate gripping engagement of the bone anchor to bone. In the illustrated embodiment, the distal shaft 118 includes an external thread 124 extending along at least a portion of the shaft for engaging bone. In the illustrated embodiment, the external thread 124 is a single lead thread that extends from a distal tip 126 of the shaft to the head portion 14, though one skilled in the art will recognize that the external thread may extend along any selected portion of the shaft and have any suitable number of leads. Other suitable bone engagement mechanisms include, but are not limited to, one or more annular ridges, multiple threads, dual lead threads, variable pitched threads and/or any conventional bone engagement mechanism.

The head portion 14 is sized and configured to receive a spinal rod or other suitable spinal connection element. The illustrative head portion 14 forms a U-shaped slot 142 or other suitable opening at the distal end of the shaft 118 for receiving a spinal rod and to couple the spinal rod to the bone anchor portion 13. The illustrative head portion 14 may be substantially similar to a head portion of a monoaxial or polyaxial screw assembly of the prior art. While the illustrative head portion 14 is sized and shaped to receive a spinal rod, one skilled in the art will recognize that the head portion 14 may be configured to accommodate any suitable spinal connection element.

Alternatively, the head portion 14 of the screw assembly can be closed at the proximal end with an opening to receive a set screw. The closed head has a side opening for receiving a spinal rod. The distal end of the side opening also has features similar to that of a U-shaped head.

As shown, the illustrative head portion 14 for receiving a rod is rigidly coupled to or integral with the anchor portion 13 to form the screw body 11, though one skilled in the art will recognize that the head portion 14 may alternatively be movably coupled to the anchor portion 13 to provide additional adjustability.

The longitudinal axis S-S of the bone anchor portion 13 preferably aligns with a longitudinal axis extending through the head portion 14. However, one skilled in the art will recognize that the head portion 14 may alternatively be offset from or extend at a selected angle relative to the anchor portion 13.

In other embodiments, a spinal connection element may be coupled to the bone anchor portion 13 by alternative coupling mechanisms in place of the illustrative head portion 14. For example, the receiving portion may alternatively comprise an offset coupling mechanism, such as a band clamp, sacral extender, or a lateral off-set connector.

The illustrative head portion 14 is also configured to movably mount the rod seat 18, which directly receives the rod 12. As described above, the rod seat 18 allows for pivoting of the rod 12 in two selected directions about a first axis X-X and/or a second axis Y-Y. The rod seat 18 of the embodiment of FIGS. 5A and 5B comprises three cooperating elements for seating the rod 12 and allowing movement of the rod relative to the screw body 11. The head portion 14 includes a recess 144 formed in the bottom of the U-shaped slot 142 for movably receiving the rod seat 18. The recess 144 preferably has a concave, cylindrical shape to allow pivoting of the rod seat 18 within the recess 144 in a first direction.

As shown, the rod seat 18 comprises a first lower element 180a disposed in the recess 142, a second lower element 180b stacked on the first lower element 180a and an upper element 181. The first lower element 180a and second lower element 180b cooperate to define a bottom portion of the rod seat 18 that allows rotation of the rod 12 about two separate axes. The rod 12 is received between the second lower element 180b and the upper element 181. A closure mechanism, illustrated as a set screw 170, secures the spinal rod 12 or other suitably configured spinal connection element within the slot 142 of the head portion 14 and locks the rod 12 and rod seat 18 in the selected orientation within and relative to the screw body 11.

The first lower element 180a facilitates pivoting of the rod 12 about one axis, which is axis Y-Y in the illustrative embodiment. The illustrative first lower element 180a is substantially half-tubular or cylindrical in shape and includes a cylindrical bottom surface 1801 configured to be received in and mate with a concave surface of the recess 144. The bottom surface is not limited to a cylindrical shape and may have any shape that is generated by one or more sweeping line segments, which may include one or more curved or straight lines, about the axis Y-Y, thus allowing rotation about the axis Y-Y. Another example is a curved surface with a grooved channel.

The recess 144 preferably has a shape that matches the bottom surface 1801 and allows sliding/rotation of the first lower element 180a relative to the screw body about axis Y-Y, which corresponds to the longitudinal axis the cylindrical body forming the first lower element 180a.

The side surfaces 1803, 1804 of the first lower element 180a may be substantially flat and abut side surfaces of the recess 144 to confine movement of the first lower element 180a to rotation about a single axis Y-Y. Alternatively, the side surfaces 1803, 1804 may have any suitable size, shape, configuration and/or orientation to facilitate controlled movement of the first lower element 180a and thus the spinal rod 12 relative to the screw body 11.

The upper surface 1802 of the first lower element 180a is sized and configured to receive the second lower element 180b and allow rotation of the second lower element 180b in a second direction relative to the first lower element 180a and the body 11 of the screw assembly 10.

The second lower element 180b has an axisymmetric mating surface that mates with the first lower element 180a to provide another rotational degree of freedom. The axisymmetric surface is symmetric about a central axis, allowing the second lower element to pivot about the central axis. The illustrative second lower element 180b includes a substantially conical-shaped bottom mating surface 1807 that is stacked on a similarly shaped recess on the upper surface 1802 of the corresponding first lower element 180a. As shown, the second lower element 180b has tapered outer walls 1807 to allow rotation of the second lower element about axis X-X. The bottom surface 1807 of the second lower element 180b and corresponding recess in the upper surface 1802 of the first lower element 180a are preferably symmetrical about axis X-X to facilitate controlled spinning of the second lower element 180b within the first lower element 180a. Alternatively, the axisymmetric bottom surface 1807 can be spherical, cylindrical, or have another suitable shape to facilitate rotation of the second lower element 180b relative to the first lower element 180a about an axis, such as the illustrative X-X axis.

The second lower element 180b further includes a substantially cylindrical upper surface 1808 for receiving the spinal rod. The upper surface 1808 preferably matches the profile of the spinal rod 12 to allow seating of the spinal rod thereon.

Figures 6A, 6B:
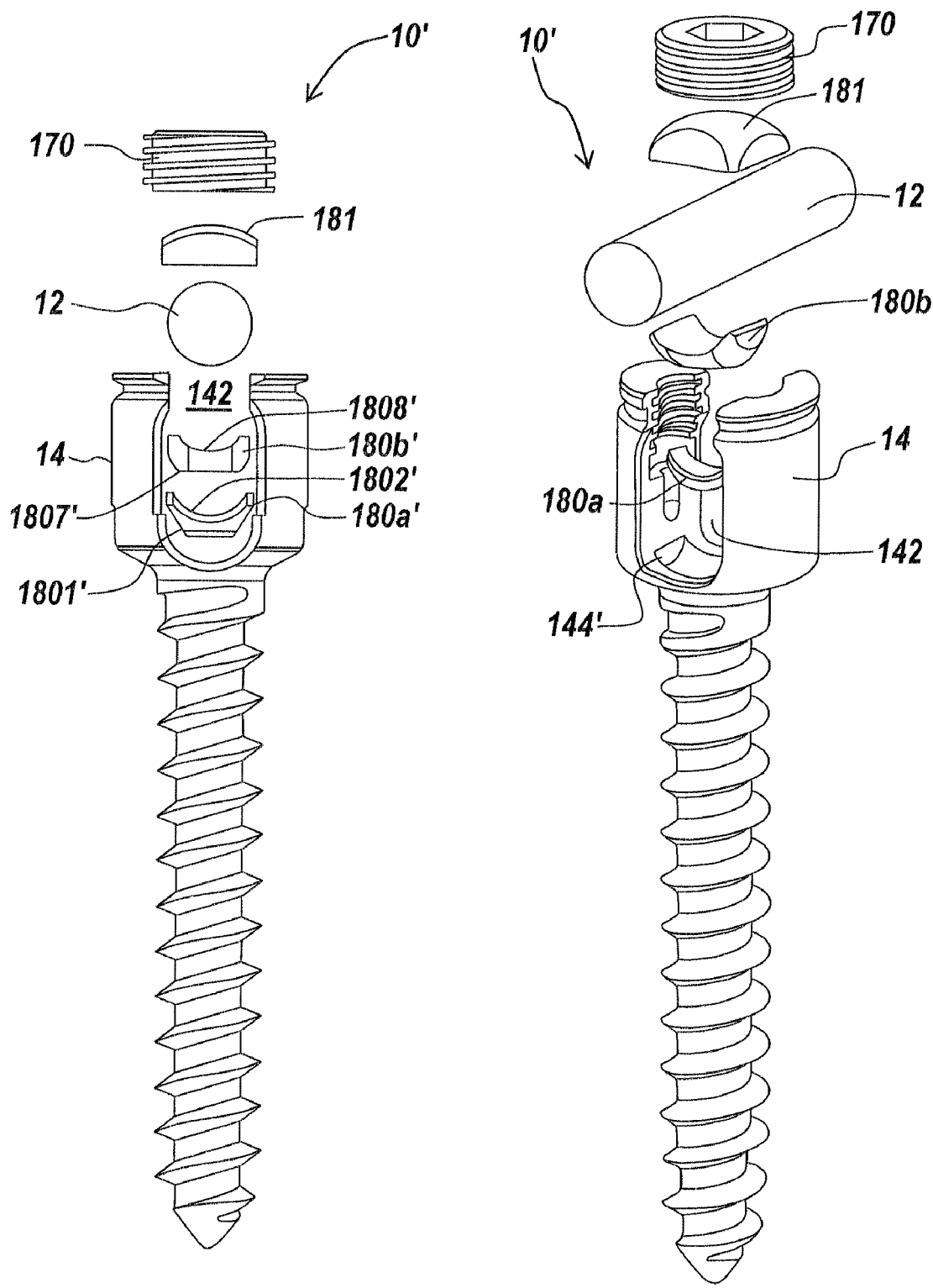
FIGS. 6A and 6B illustrate a biaxial bone screw assembly according to another embodiment of the invention.

According to another embodiment of the invention, shown in FIGS. 6A and 6B, the position or shape of the first lower element 180*a* and the second lower element 180*b* can be exchanged. For example, in the biaxial bone screw assembly 10' of FIGS. 6A and 6B, the first lower element 180*a'* has a conical shape to facilitate rotation about axis S-S. The second lower element 180*b'* stacked on the first lower element 180*a'* has a cylindrical shape to facilitate rotation about axis X-X. Preferably, the bottom surface 1801' of the first lower element 180*a'* and the opposing distal end slot 142 in the screw head have mating conical shapes that allows rotation about Axis S-S. In addition, the top surface 1802' of the first lower element 180*a'* and opposing bottom surface 1807' of the second lower element 180*b'* have mating cylindrical shape that allows rotation about X-X.

In the illustrative embodiment, the top element 181 of the spinal rod has a flat bottom surface 1812 and a curved, substantially spherical upper surface 1814 to allow for pivoting of the rod seat 18 about both axes X-X and Y-Y. Alternatively, the bottom surface 1812 may be cylindrical. One skilled in the art will recognize that the top element 181 may have any suitable size, shape and configuration.

Alternatively, the top element 181 may comprise two separate elements, including an axisymmetrical mating surface and a cylindrical mating surface to facilitate adjustment of the spinal rod 12 relative to the body of the screw.

The rod seat 18 may be configured to allow spinning of the spinal rod 12 about the axis R-R. Alternatively, the second lower element 180*b* and/or the top element 181 may be configured to prevent rotation of the spinal rod 12 about the axis when the spinal rod 12 is seated in the rod seat.

After pivoting the spinal rod 12 about one or both selected axes in a selected direction relative to the bone anchor by a selected degree, preferably between 0° and 90°, a user can lock the orientation of the rod 12 relative to the screw body 11 by inserting a closure mechanism, such as the set screw 170. The closure mechanism secures a spinal rod 12 or other suitably configured spinal connection element within the U-shaped slot 142 of the head portion and locks the rod in the selected orientation within and relative to the screw body. In the illustrative embodiment, distal advancement of the closure mechanism into engagement with the spinal rod 12 in the slot 142 seats the spinal rod in the seat 18. Other suitable closure mechanisms may be employed to secure the spinal connection element to the assembly and/or to lock the orientation of the bone anchor relative to the receiving portion.

The first lower element 180*a* and second lower element 180*b* may be movably retained in the head portion through any suitable means. For example, as shown in FIGS. 7-10, a retaining pin 191 may extend through the first lower element 180*a* and second lower element 180*b* and into the body 11 of the screw to movably couple the lower portion 180*a*, 180*b* of the rod seat 18 to the screw body 11. As shown in FIGS. 8A and 8B, the first lower element 180*a* may include a slot 185 extending substantially parallel to the axis R-R and perpendicular to the axis X-X for receiving the retaining pin 191. The retaining pin 191 slides within the slot during rotation of the first lower element within the recess 144. The slot and pin facilitate rotation while preventing movement of the first lower element in other directions.

As shown in FIGS. 9A-9C, the second lower element 180*b* includes a longitudinally extending hole 187 for receiving and seating the alignment pin 191. The hole 187 aligns with the axis X-X, such that the second lower element spins about the alignment pin 191. The hole 187 may comprise a lower portion 187*a* having a diameter corresponding to the diameter of the body 193 of the retaining pin 191, shown in FIG. 10. The hole 187 includes an upper portion 187 for seating the head 195 of the retaining pin 191 to prevent the second lower element 180*b* from decoupling.

According to another embodiment of the invention, the side surfaces 1803, 1804 of the first lower element 180*a* may have slots for slidably receiving protrusions formed in the side walls of the recess 144 to allow controlled rotation while retaining the first lower element 180*a* within the U-shaped slot 142. Alternatively, the side surfaces 1803, 1804 may have protrusions that are slidably received in corresponding slots on the side walls of the recess 144.

In another embodiment, the outer bottom surface 1807 of the conical-shaped second lower element 180*b* may include a horizontal slot or pin(s) configured to cooperate with a corresponding pin(s) or slot on the upper surface 1802 of the first lower element 180*a*. The cooperating pin(s) and slot allow spinning of the second lower element 180*b* within the first lower element 180*a*.

One skilled in the art will recognize that any suitable means for coupling the first and second lower elements 180*a* and 180*b* to each other and/or to the screw body while allowing controlled relative adjustment may be used.

According to another embodiment of the invention, shown in FIGS. 11A and 11B, the rod seat 18 of an adjustable bone screw assembly 10" may comprise a single lower element 180 for allowing controlled adjustment of the spinal rod orientation relative to the body 11. The single lower element 180 defines both the surface 1801 that is received and moves relative to the head portion 14, as well as the surface 1808 that receives the spinal rod. For example, the rod seat 18 may alternatively comprise only the conical-shaped or other axisymmetric-shaped second lower element 180*b* disposed directly in a corresponding recess 144" in the slot 142 of the head portion 14 to allow rotation of the spinal rod 12 received by the second lower element 180*b* about only the X-X axis only, as shown in FIGS. 11A and 11B.

Alternatively, the rod seat 18 may comprise only the cylindrical-shaped first lower element 180*a* having a cylindrical lower surface 1801 for allowing pivoting about the Y-Y axis and an upper surface 1802 that is configured to receive the spinal rod 12 without a separately movable intermediate element (i.e., the second lower element 180*b*).

Figure 12A:
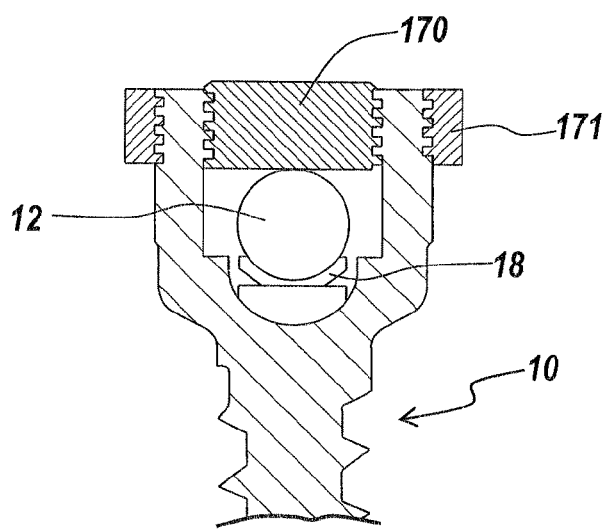
FIG. 12A illustrates one embodiment of a set screw used in a biaxial bone screw assembly of an illustrative embodiment of the invention.
Figure 12B:
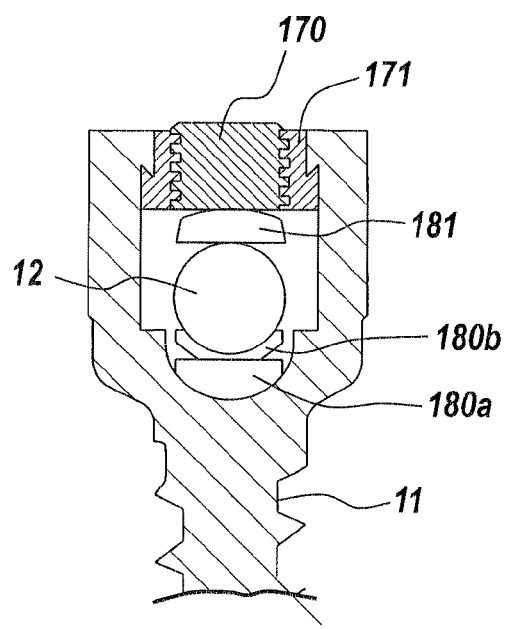
FIG. 12B illustrates another embodiment of a set screw used in a biaxial bone screw assembly of an illustrative embodiment of the invention.
Figure 13:
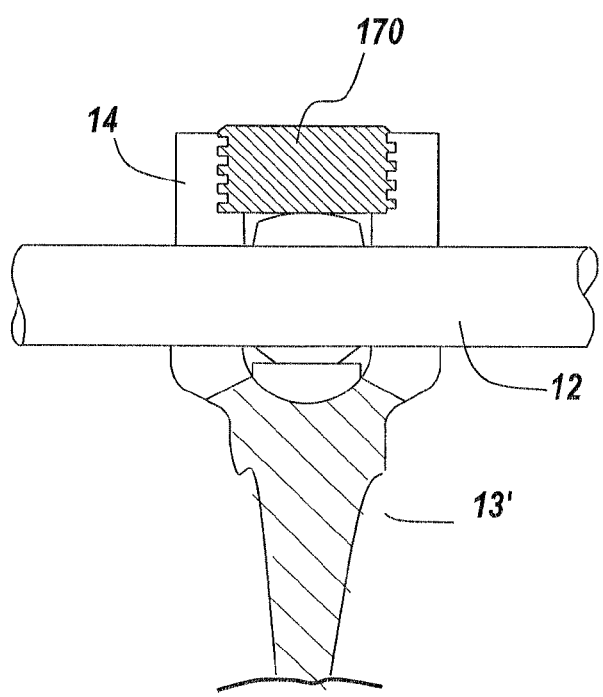
FIG. 13 illustrates a biaxial bone screw assembly of an illustrative embodiment of the invention including a tapered anchor portion.

The closure mechanism 170 may have any suitable size, shape, configuration and means for securing the rod and rod seat in a selected orientation relative to the screw body 11. The closure mechanism 170 may be secured to the screw body 11 through any suitable means, including and exterior fixation device and an interior fixation devices. FIGS. 12A and 12B illustrate two suitable means for securing a set screw 170 against the rod seat 18 and spinal rod 12. For example, as shown in FIG. 12A, an outside nut 171 may encircle the proximal end of the head portion 14 to secure the set screw 170 and lock the spinal rod 12 in a selected configuration relative to the screw body 11. According to an alternate embodiment, shown in FIG. 12B, a typhoon cap 176 may be disposed inside the head portion 14 to lock the set screw 170 in position, thereby locking the orientation of the spinal rod 12 relative to the screw body 11. One skilled in the art will recognize that any suitable means for locking the spinal rod in a selected position and orientation relative to the screw body 11 may be used.

According to another embodiment, the top element 181 of the rod seat 18 may be retained in the set screw 170 to avoid assembling multiple parts during surgery.

The anchor portion 13 of the screw assembly can have any suitable size, configuration and shape and is not limited to a constant-diameter anchor portion as required in polyaxial screws of the prior art. According to one embodiment of the invention, shown in FIG. 13, the anchor portion 13' of the screw assembly 10 may be tapered to provide a larger diameter near the head portion 14. The use of a unitary screw body with an adjustable rod seat facilitates an anchor portion 13' with a varying diameter. In contrast, in polyaxial screws of the prior art, the screw diameter is limited by the diameter of the spherical top of the anchor disposed in the head portion. However, the biaxial screw assembly 10 of the illustrative embodiment of the invention places no limitation on the anchor diameter and shape.

In addition, the biaxial screw assembly 10 of the illustrative embodiments of the invention allows for a reduction in the rod-to-bone distance when the biaxial bone screw assembly 10 is employed to secure a spinal rod to bone. During use, a force is applied on a rod inserted in the screw assembly at a distance D away from the bone surface (the rod-to-bone distance). The force creates a moment on the bone screw, which is directly proportional to the distance D. The bone screw assembly 10 of the illustrative embodiments of the invention preferably reduces the rod-to-bone distance, relative to bone screw assemblies of the prior art, thereby reducing the applied moment on the screw. A smaller moment on the screw reduces the likelihood of screw-bone loosening and screw breakage.

Figure 14:
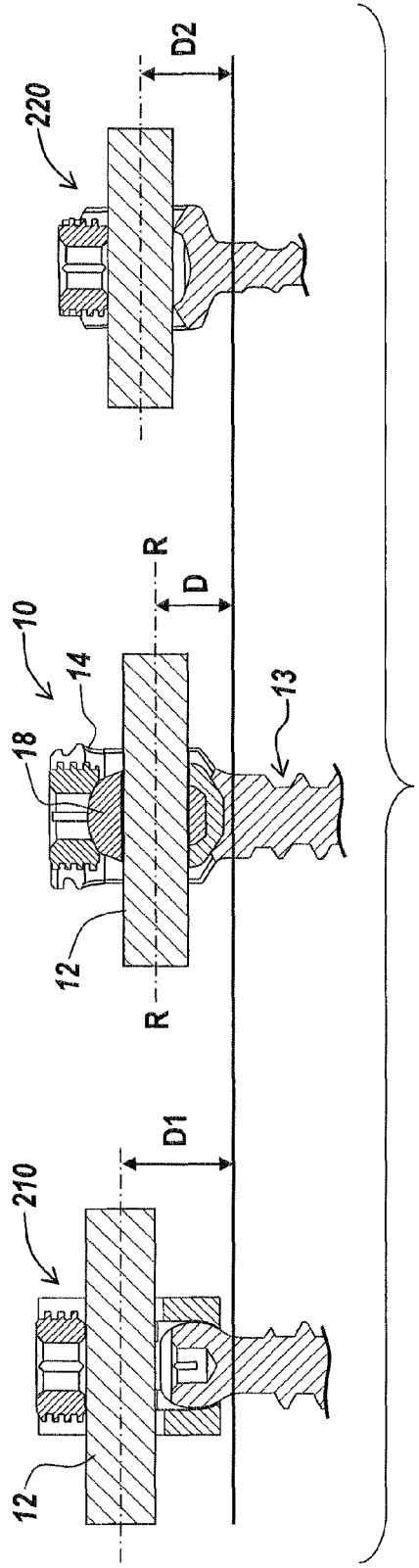
FIG. 14 illustrates a biaxial bone screw assembly of an illustrative embodiment of the invention, a polyaxial bone screw assembly of the prior art and a monoaxial bone screw assembly of the prior art, comparing a rod-to-bone distance between the three bone screw assemblies.

For example, FIG. 14 illustrates a comparison between the rod-to-bone distance D of the biaxial screw assembly 10 of the illustrative embodiment of the invention compared with a rod-to-bone distance D1 of a polyaxial screw assembly 210 of the prior art and a rod-to-bone distance D2 of a monoaxial screw assembly 220 of the prior art. For example, the illustrative biaxial bone screw assembly 10 has a rod-to-bone distance D of between about 5 and 7 millimeters. As illustrated the rod-to-bone distance D of the illustrative embodiment is about 5.58 millimeters. The rod-to-bone distance D1 of a monoaxial screw assembly 220 is also between about 5 and 7 millimeters. As illustrated the rod-to-bone distance of D1 of the illustrative embodiment is about 6.90 millimeters. In contrast, the rod-to-bone distance D2 of the polyaxial screw is larger, with distance between about 7 to 9 millimeters. As illustrated the rod-to-bone distance of D2 of the illustrative embodiment is about 8.77 millimeters. Hence, the biaxial screw assembly 10 provides a similar rod-to-bone distance to that of monoaxial screw assembly 220, yet the biaxial screw assembly provides additional degrees-of-freedom to adjust the orientation of the spinal rod relative to the screw assembly.

Figure 15:
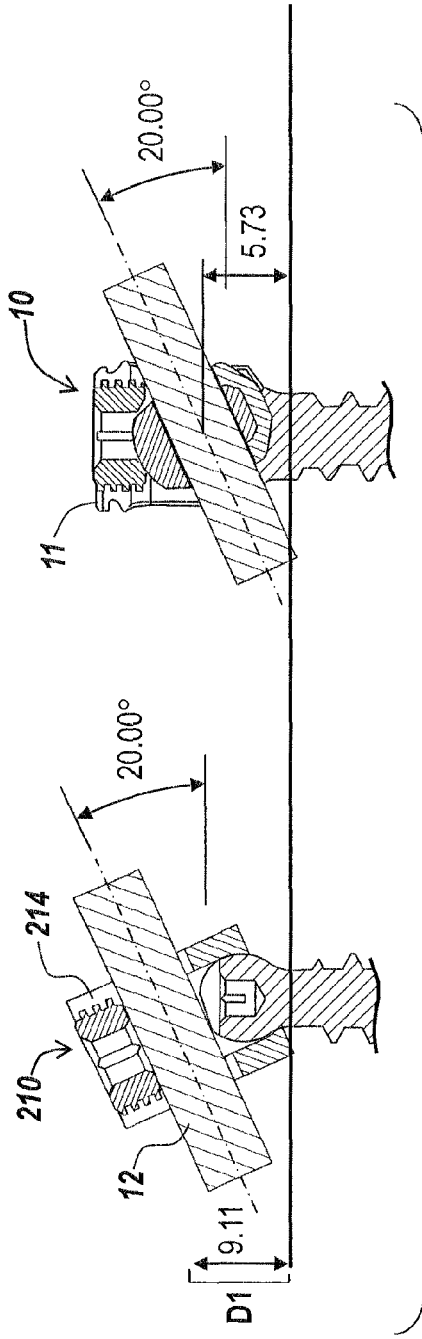
FIG. 15 illustrates biaxial bone screw assembly of an illustrative embodiment of the invention and a polyaxial bone screw assembly of the prior art when the spinal rods are rotated by 20 degrees relative to the respective anchor portions.

FIG. 15 illustrates a comparison of the rod-to-bone distance of the biaxial screw assembly of an illustrative embodiment of the invention, and a polyaxial screw of the prior art after rotation of the spinal rod 12 by about 20 degrees. As shown, when the rod 13 inserted in a polyaxial screw head 214 is rotated 20 degrees, the moving head of the polyaxial screw assembly 210 increases the rod-to-bone distance D1 to 9.11 millimeters, while the biaxial screw assembly 10 of the illustrative embodiment of the invention retains a similar rod-to-bone distance D of about 5.73 millimeters when the rod 12 is rotated 20 degrees relative to the screw body 11, thereby minimizing breaks and loosening.

The illustrative adjustable bone screw assembly may be used to facilitate connection between two vertebrae in the spinal column. A surgeon may insert a spinal rod into a first bone screw assembly anchored to a first vertebra, and then adjust the orientation of the spinal rod about one, two or more axes, as necessary, to align the spinal rod with a second bone screw assembly anchored to a second vertebra. Another portion of the spinal rod may be inserted into the second bone screw assembly. The second bone screw assembly may also permit adjustment of the orientation of the spinal rod in one, two or more selected directions, as necessary. After proper alignment, the spinal rods are locked in the selected positions relative to the bone screw assemblies to connect the two vertebrae.

The components of the biaxial bone screw assembly of the illustrative embodiments of the invention may be manufactured from any suitable biocompatible material, including, but not limited to, metals and metal alloys such as titanium and stainless steel, polymers and/or ceramics. The components may be manufactured from the same or different materials though manufacturing processes known in the art.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. A bone screw assembly comprising: a bone anchor having a distal shaft extending along a longitudinal axis; a proximal head portion fixed relative to the bone anchor; and a rod seat disposed within the proximal head portion for seating a spinal rod, wherein the rod seat comprises: a first lower element confined to rotate about a first axis in a first direction relative to the proximal head portion; and a second lower element stacked on the first lower rod seat element for seating a spinal rod and confined to rotate about a second axis in a second direction relative to the first lower element, wherein the first axis is substantially perpendicular to a longitudinal axis of the spinal rod and the longitudinal axis of the distal shaft, and wherein the second axis aligns with the longitudinal axis of the distal shaft.

2. The bone screw assembly of claim 1, wherein the proximal head portion includes a recess for receiving the first lower element.

3. The bone screw assembly of claim 1, wherein the first lower element has a cylindrical bottom surface that curves in the first direction.

4. The bone screw assembly of claim 1, wherein the first lower element has a bottom surface that is generated by sweeping a line segment about the first axis, thus allowing rotation about the first axis.

5. The bone screw assembly of claim 1, wherein the second lower element has a bottom surface that is axisymmetric about the second axis.

6. The bone screw assembly of claim 5, wherein the second lower element has a conical bottom surface.

7. The bone screw assembly of claim 1, wherein the first lower element has bottom surface that is axisymmetric about the second axis and the second lower element has a bottom surface abutting a top surface of the first lower element, wherein the bottom surface of the second lower element is generated by sweeping a line segment about the first axis, thus allowing rotation about the first axis.

8. The bone screw assembly of claim 1, wherein the first lower element includes a slot extending in the first direction and the second lower element includes an opening aligned with the second axis and the rod seat further comprises a retaining pin extending through the first lower element, the second lower element and into the head portion to movably couple the first lower element and the second lower element to the head portion.

9. The bone screw assembly of claim 1, wherein the second lower element includes an opening aligned with the second axis and the rod seat further comprises a retaining pin extending through the second lower element into the first element head portion to movably couple the second lower to the first lower element.

10. The bone screw assembly of claim 1, wherein the second lower element includes a recess for receiving the spinal rod.

11. The bone screw assembly of claim 1, wherein the rod seat further comprises a top element having a spherical top surface, and the spinal rod is received between a bottom surface of the top element and the second lower element.

12. The bone screw assembly of claim 1, wherein the distal shaft of the bone anchor is tapered.

13. A bone anchor assembly comprising: a bone anchor having a distal shaft extending along a longitudinal axis and a proximal head; a first lower rod seat element disposed in the proximal head and configured to pivot about a second axis; and a second lower rod seat element stacked on the first lower rod seat element for seating a spinal rod, wherein the second lower rod seat element includes a top surface for receiving the spinal rod and an axisymmetric bottom surface that is symmetric about the longitudinal axis to pivot about the longitudinal axis; and wherein the second axis is substantially perpendicular to a longitudinal axis of the spinal rod and the longitudinal axis of the distal shaft.

14. The bone anchor assembly of claim 13, wherein the axisymmetric bottom surface is conical-shaped.

15. The bone anchor assembly of claim 13, wherein the first lower rod seat element has a cylindrical bottom surface disposed in a recess of the proximal head.

16. The bone anchor assembly of claim 15, wherein the cylindrical bottom surface of the first lower rod seat element curves in a selected direction to allow pivoting of the first lower rod seat element and the spinal rod in the selected direction relative to the bone anchor.

17. A bone anchor assembly, comprising: a bone anchor portion having a distal shaft extending along a longitudinal axis; a head portion fixed to a proximal end of the bone anchor portion; and a seat element disposed in the head portion for seating a spinal rod, the seat element comprising a first lower rod seat element configured to rotate about a first axis, and a second lower rod seat element stacked on the first lower rod seat element and configured to rotate about a second axis, wherein the first axis is substantially perpendicular to a longitudinal axis of the spinal rod and the longitudinal axis of the distal shaft; and wherein the second axis aligns with the longitudinal axis of the distal shaft.

* * * * *